(12) United States Patent
Creaven (10) Patent No.: US 8,142,733 B2
(45) Date of Patent: Mar. 27, 2012

(54) SENSOR-DISPENSING DEVICE AND MECHANISM FOR EXTRACTING SENSOR

(75) Inventor: John P. Creaven, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 806 days.

(21) Appl. No.: 11/791,460

(22) PCT Filed: Oct. 19, 2005

(86) PCT No.: PCT/US2005/037364
§ 371 (c)(1),
(2), (4) Date: Apr. 13, 2007

(87) PCT Pub. No.: WO2006/047135
PCT Pub. Date: May 4, 2006

(65) Prior Publication Data
US 2008/0021296 A1      Jan. 24, 2008

Related U.S. Application Data

(60) Provisional application No. 60/620,834, filed on Oct. 21, 2004.

(51) Int. Cl.
*G01N 1/00* (2006.01)
(52) U.S. Cl. ....... 422/401; 422/63; 422/82.01; 422/417; 422/430; 422/561; 221/4; 221/232; 221/259; 221/271; 221/268
(58) Field of Classification Search .................. None
See application file for complete search history.

(56) References Cited

U.S. PATENT DOCUMENTS

| 3,797,488 A | 3/1974 | Hurschman et al. | 604/136 |
| 4,449,529 A | 5/1984 | Burns et al. | 606/182 |
| 4,469,110 A | 9/1984 | Slama | 128/770 |
| 4,517,978 A | 5/1985 | Levin et al. | 606/182 |

(Continued)

FOREIGN PATENT DOCUMENTS

EP     1 321 769     6/2003

(Continued)

OTHER PUBLICATIONS

Written Opinion of the International Searching Authority corresponding to co-pending International Patent Application No. PCT/US2005/037364, European Patent Office, dated Jan. 26, 2006, 5 pages.

(Continued)

*Primary Examiner* — Sally Sakelaris
(74) *Attorney, Agent, or Firm* — Nixon Peabody LLP (57) ABSTRACT

A cartridge assembly is adapted to be used in a sensor-dispensing device. The cartridge assembly comprises an end cap, a disposable cartridge and a sealing mechanism. The end cap includes one opening. The disposable cartridge comprises an outer and inner cartridge. The inner cartridge contains sensors arranged in a stack therein. Each of the sensors carries a reagent sufficient to produce a signal in response to the analyte concentration in a fluid. The outer cartridge forms an opening of sufficient dimensions to permit a sensor to pass through the opening. The outer cartridge includes a holding mechanism that holds at least one of the sensors in place during movement of the inner cartridge. The sealing mechanism is adapted to form a substantially moisture-tight seal.

33 Claims, 8 Drawing Sheets

U.S. PATENT DOCUMENTS

| | | | | |
|---|---|---|---|---|
| 4,627,445 | A | 12/1986 | Garcia et al. | 128/770 |
| 4,637,403 | A | 1/1987 | Garcia et al. | 128/770 |
| 4,735,203 | A | 4/1988 | Ryder et al. | 606/182 |
| 4,787,398 | A | 11/1988 | Garcia et al. | 128/770 |
| 4,911,344 | A | 3/1990 | Kahler | 221/228 |
| 4,990,154 | A | 2/1991 | Brown et al. | 606/182 |
| 5,074,872 | A | 12/1991 | Brown et al. | 606/182 |
| 5,196,025 | A | 3/1993 | Ranalletta et al. | 600/583 |
| 5,231,993 | A | 8/1993 | Haber et al. | 128/770 |
| 5,244,116 | A | 9/1993 | Leo | |
| 5,267,963 | A | 12/1993 | Bachynsky | 604/134 |
| 5,279,294 | A | 1/1994 | Anderson et al. | 128/633 |
| 5,304,193 | A | 4/1994 | Zhadanov | 600/585 |
| 5,318,583 | A | 6/1994 | Rabenau et al. | 606/182 |
| 5,320,607 | A | 6/1994 | Ishibashi | 604/115 |
| 5,350,392 | A | 9/1994 | Purcell et al. | 606/182 |
| 5,527,334 | A | 6/1996 | Kanner et al. | 600/583 |
| 5,575,777 | A | 11/1996 | Cover et al. | 604/198 |
| 5,628,764 | A | 5/1997 | Schraga | 606/181 |
| 5,741,288 | A | 4/1998 | Rife | 606/181 |
| 5,868,772 | A | 2/1999 | LeVaughn et al. | 606/181 |
| 5,916,230 | A | 6/1999 | Brenneman et al. | 606/181 |
| 5,951,492 | A | 9/1999 | Douglas et al. | 600/583 |
| 5,951,493 | A | 9/1999 | Douglas et al. | 600/583 |
| 5,954,738 | A | 9/1999 | LeVaughn et al. | 606/181 |
| 5,971,941 | A | 10/1999 | Simons et al. | 600/583 |
| 6,022,366 | A | 2/2000 | Schraga | 606/181 |
| 6,048,352 | A | 4/2000 | Douglas et al. | 606/181 |
| 6,050,977 | A | 4/2000 | Adams | 604/195 |
| 6,090,078 | A | 7/2000 | Erskine et al. | 604/198 |
| 6,093,156 | A | 7/2000 | Cunningham et al. | 600/57 |
| 6,099,484 | A | 8/2000 | Douglas et al. | 606/181 |
| 6,152,942 | A | 11/2000 | Brenneman et al. | |
| 6,210,421 | B1 | 4/2001 | Bocker et al. | 606/182 |
| 6,231,531 | B1 | 5/2001 | Lum et al. | 600/573 |
| 6,306,152 | B1 | 10/2001 | Verdonk et al. | 606/182 |
| 6,322,574 | B1 | 11/2001 | Lloyd et al. | |
| 6,364,889 | B1 | 4/2002 | Kheiri et al. | |
| 6,409,740 | B1 | 6/2002 | Kuhr et al. | 606/182 |
| 6,432,120 | B1 | 8/2002 | Teo | |
| 6,451,040 | B1 | 9/2002 | Purcell | 606/181 |
| 6,514,270 | B1 | 2/2003 | Schraga | |
| 6,537,292 | B1 | 3/2003 | Lee | |
| 6,602,268 | B2 | 8/2003 | Kuhr et al. | 606/181 |
| 6,607,543 | B2 | 8/2003 | Purcell et al. | 606/181 |
| 6,997,343 | B2 * | 2/2006 | May et al. | 221/232 |
| 7,582,262 | B2 * | 9/2009 | Funke et al. | 422/430 |
| 2002/0057993 | A1 | 5/2002 | Maisey et al. | 422/82.01 |
| 2002/0076349 | A1 | 6/2002 | Aitken et al. | 422/58 |
| 2002/0104849 | A1 | 8/2002 | Giruad | 221/270 |
| 2003/0002387 | A1 | 1/2003 | Bottwein et al. | 366/273 |
| 2003/0089730 | A1 | 5/2003 | May et al. | 221/232 |
| 2003/0116583 | A1 | 6/2003 | Pugh | 221/268 |
| 2003/0186446 | A1 | 10/2003 | Pugh | 436/46 |
| 2003/0191415 | A1 | 10/2003 | Moerman et al. | 600/584 |
| 2003/0212345 | A1 | 11/2003 | McAllister et al. | 600/584 |
| 2003/0223906 | A1 | 12/2003 | McAllister et al. | 422/58 |
| 2004/0178216 | A1 | 9/2004 | Brickwood et al. | |
| 2008/0021296 | A1 | 1/2008 | Creaven | |

FOREIGN PATENT DOCUMENTS

| | | |
|---|---|---|
| EP | 1 416 274 | 5/2004 |
| EP | 1 806 588 | 11/2007 |
| WO | WO03/042691 | 5/2003 |
| WO | WO03/083469 | 10/2003 |
| WO | WO2006/046701 | 4/2006 |

OTHER PUBLICATIONS

International Search Report corresponding to co-pending International Patent Application No. PCT/US2005/037364, European Patent Office, dated Jan. 26, 2006, 5 pages.

* cited by examiner

SENSOR-DISPENSING DEVICE AND MECHANISM FOR EXTRACTING SENSOR

CROSS-REFERENCE TO RELATED APPLICATION

This application claims priority to U.S. Provisional Application No. 60/620,834, filed on Oct. 21, 2004.

FIELD OF THE INVENTION

The invention generally relates to a sensor-dispensing device and a mechanism for extracting a test sensor from the device.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. Additionally, determining glucose in body fluids is important to diabetic individuals who must frequently check the glucose level in their body fluids to regulate the glucose intake in their diets. While the remainder of the disclosure herein will be directed towards glucose determination, it is to be understood that the methods of this invention may be used for determining other analytes on selection of an appropriate enzyme.

The results of such tests can be used to determine how much, if any, insulin or other medication needs to be administered. In one type of blood glucose testing system, test sensors are used to test a sample of blood.

A test sensor typically contains biosensing or reagent material that will react with blood glucose. A testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the test sensor. The current generated by the electrochemical reaction is converted into a measurement that is indicative of the analyte level in the fluid being tested.

To couple the electrical signals produced at the test sensor contacts to monitoring equipment, the sensors need to be inserted into sensor holders prior to the sensor end being placed into the fluid being tested. The holders have corresponding mating contacts that become coupled to the contacts on the test sensor when the sensor is properly inserted into the holder. Consequently, the holders act as an interface between the test sensor and monitoring equipment that accumulates and/or analyzes the test results.

Most test sensors need to be maintained at an appropriate humidity level prior to being used so as to insure the integrity of the reagent materials in the sensor. Test sensors can be packaged individually in tearaway packages so that they can be maintained at the proper humidity level. For instance, blister-type packaging methods may be used. In this connection, the packages can include desiccant material to maintain the proper humidity in the package. For a person to use an individual test sensor for testing an analyte, the package may be opened by tearing the seal. Alternatively, some packages require the user to exert force against one side of the package resulting in the test sensor bursting or rupturing the foil on the other side. As can be appreciated, the opening of these packages can be difficult. Moreover, once the package is opened, the user needs to be sure that the test sensor is not damaged or contaminated as it is being placed into the sensor holder and used to test the fluid sample.

In certain sensor-dispensing devices, a stack of disposable test sensors is provided within a cartridge and the stack is pushed or urged towards a test station where testing occurs. A pushing mechanism is inserted into a first opening on one end of the cartridge, through which the mechanism contacts the stack of sensors. Typically, the pushing mechanism moves the top most sensor in the stack through a second opening that is usually located on the opposite end of the cartridge from the first opening toward a testing station. Therefore, the use of a pushing mechanism requires the presence of two openings in the cartridge. Cartridges having two openings may present problems with sealing the cartridge in order to preserve the shelf-life of the remaining sensors within the cartridge.

In some sensor-dispensing devices, the mechanism for moving a sensor from a stack of test sensors is located in the disposable cartridge that houses the stack of sensors. In other words, every time the empty cartridge is discarded, the mechanism for moving the sensor is also discarded, thereby raising the cost of replacing the cartridge.

In some sensor dispensing devices that use disposable cartridges, the mechanisms that seal the sensor within the cartridge and permit the sensor to be removed from the cartridge are designed to be physically attached to the cartridge. Therefore, every time the cartridge is depleted of sensors and must be replaced, the sealing mechanisms must also be replaced, thereby adding to the cost of replacing the cartridge.

Accordingly, it would be desirable to have a sensor-dispensing device and a mechanism for extracting a sensor that overcomes the problems discussed above.

SUMMARY OF THE INVENTION

According to one embodiment, a sensor-dispensing device is adapted to determine an analyte concentration of a fluid. The device comprises a cartridge assembly and a gripping mechanism. The cartridge assembly includes an end cap, a disposable cartridge and a sealing mechanism. The disposable cartridge comprises an outer cartridge and an inner cartridge. The inner cartridge contains a plurality of sensors arranged in a stack therein. The outer cartridge includes a holding mechanism that holds at least one of the sensors in place during movement of the inner cartridge. The sealing mechanism is adapted to form a substantially moisture-tight seal so as to protect the sensors within the inner cartridge from atmospheric moisture. The gripping mechanism is adapted to grip a sensor and pull the sensor from the stack through the opening in the outer cartridge to a dispensed position. The outer cartridge forms an opening of sufficient dimensions to permit a sensor and the gripping mechanism to pass therethrough.

According to another embodiment, a cartridge assembly is adapted to be used in a sensor-dispensing device. The sensor-dispensing device is adapted to determine the analyte concentration of a fluid. The cartridge assembly comprises an end cap, a disposable cartridge and a sealing mechanism. The disposable cartridge comprises an outer cartridge and an inner cartridge. The inner cartridge contains a plurality of sensors arranged in a stack therein. Each of the plurality of sensors carries a reagent sufficient to produce a signal in response to the analyte concentration in the fluid. The outer cartridge forms an opening of sufficient dimensions to permit a sensor to pass through the opening. The outer cartridge includes a holding mechanism that holds at least one of the sensors in place during movement of the inner cartridge. The sealing mechanism is adapted to form a substantially moisture-tight seal so as to protect the sensors within the inner cartridge from atmospheric moisture.

According to one method, a sensor-dispensing device is adapted to handle a sensor pack containing a plurality of sensors. A sensor-dispensing device is provided that includes a cartridge assembly and a gripping mechanism. The cartridge assembly includes an end cap, a disposable cartridge and a sealing mechanism. The disposable cartridge comprises an outer cartridge and an inner cartridge. The inner cartridge contains a plurality of sensors arranged in a stack therein. The outer cartridge includes a holding mechanism that holds at least one of the sensors in place during movement of the inner cartridge. The outer cartridge forms an opening of sufficient dimensions to permit a sensor and the gripping mechanism to pass therethrough. The sealing mechanism is adapted to form a substantially moisture-tight seal so as to protect the sensors within the inner cartridge from atmospheric moisture. The gripping mechanism is advanced so as to move the sealing mechanism to an open position and to contact one of the plurality of test sensors. The test sensor is pulled via the gripping mechanism through the opening of the cartridge assembly. A fluid with an analyte is placed on the test sensor. The concentration of the analyte is determined.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE ILLUSTRATED EMBODIMENTS

The present invention includes a disposable cartridge that contains a plurality of test sensors. The plurality of test sensors is used to determine concentrations of analytes. Analytes that may be measured using the present invention include glucose, lipid profiles (e.g., cholesterol, triglycerides, LDL and HDL), microalbumin, hemoglobin A1C, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, or other body fluids like ISF (interstitial fluid) and urine.

Figure 1:
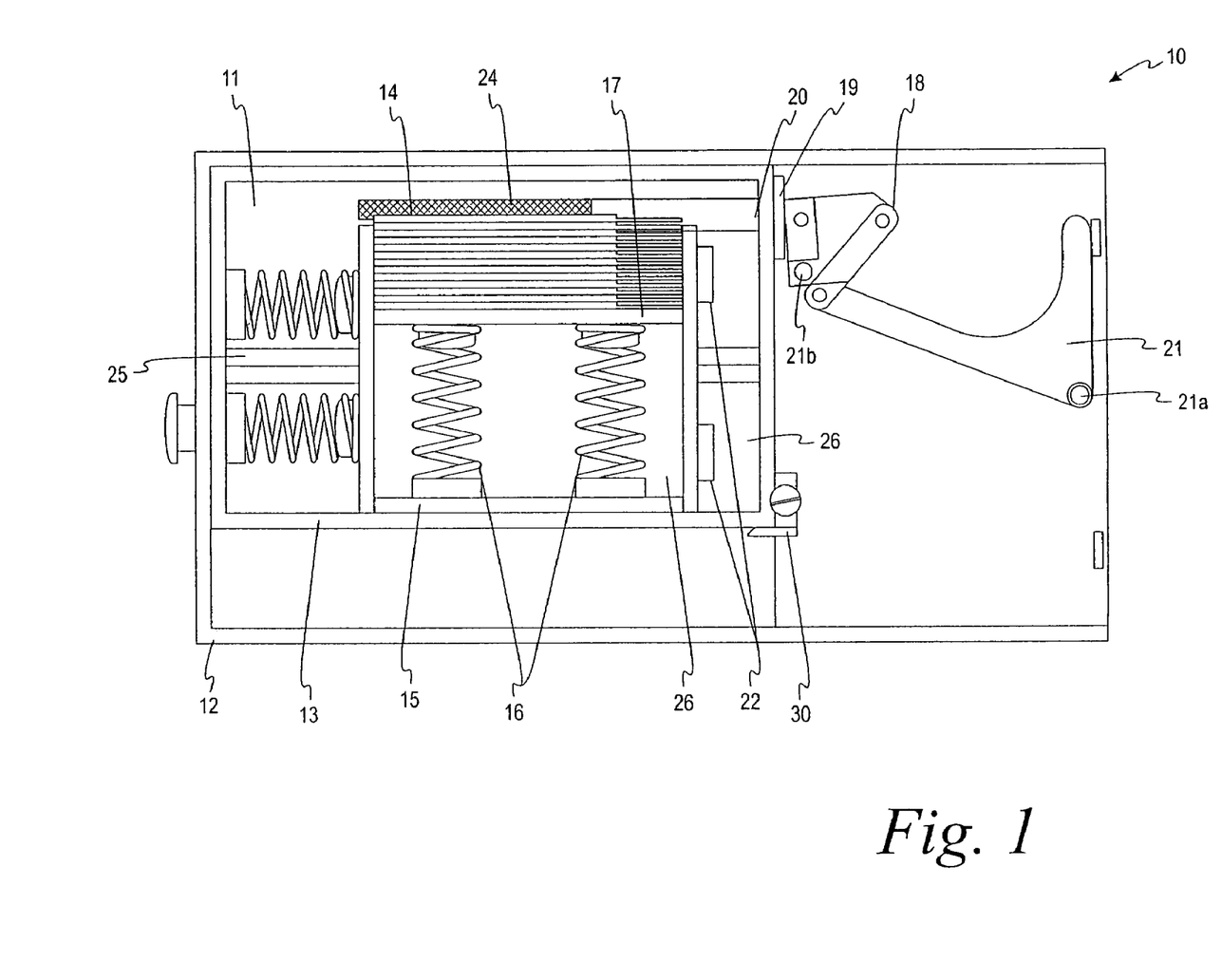
FIG. 1 is a front view of a cartridge assembly according to one embodiment of the invention.

Referring to the drawings, a cartridge assembly 10 in FIG. 1 is shown that is adapted to be used in a sensor-dispensing device. The cartridge assembly 10 is a substantially moisture-proof and air-tight device. The cartridge assembly 10 of FIG. 1 comprises a disposable cartridge 11 and an end cap 12. The cartridge 11 comprises an outer cartridge 13 and an inner cartridge 15. The inner cartridge comprises a plurality of test sensors 14 and a mechanical mechanism 16. The end cap comprises at least one sealing mechanism 18. The cartridge 11 is adapted to be disposable after each of the plurality of test sensors 14 has been used. After each of the plurality of test sensors 14 has been used, the cartridge 11 may be disassembled from the end cap 12 and replaced with a second cartridge that includes a plurality of unused test sensors.

Referring to FIG. 1, the outer cartridge 13 contains an opening 20 through which the test sensors 14 exit the cartridge 11. In the closed, i.e., sealed position, the opening 20 is sealed using at least one sealing mechanism 18. The sealing mechanism 18 prevents or inhibits air and moisture from entering into the interior of the cartridge 11 that contains a plurality of test sensors 14 within the inner cartridge 15. The opening 20 extends from the outer cartridge 13 to the inner cartridge 15. The opening 20 is sized to allow the plurality of test sensors 14 to move therethrough one at a time and eventually exit the inner cartridge 15 and outer cartridge 13. Specifically, the plurality of test sensors 14, one at a time, exits the inner cartridge 15 and outer cartridge 13 via the opening 20.

The sealing mechanism 18 contained within the end cap 12, comprises a seal door 19 that covers the opening 20 when the door is in the sealed position as shown in FIG. 1. The seal door 19 may rotate along an axis to permit the door to seal the opening 20 in cases where the door 19 may become misaligned with the opening 20 during operation. The sealing mechanism 18 further comprises a linkage mechanism 21 that facilitates the movement of the seal door 19 during the sealing and unsealing of the opening 20. The linkage mechanism 21 comprises at least two fixed points, designated in FIG. 1 as 21a and 21b. The fixed points, 21a and 21b, maintain the linkage mechanism in place during the movement of the seal door 19.

The inner surface of the outer cartridge 13 comprises one or more members, designated as 22 in FIG. 1. The members 22 stop the movement of the inner cartridge 15 when they come into contact with its outer surface and prevent the further movement of the inner cartridge 15 in the direction of the opening 20. In addition, the space created between the inner cartridge and outer cartridge when the members 22 contact the inner cartridge may be used to house desiccant material 26.

The outer cartridge 13 comprises a holding mechanism or feature 24 that holds the upper most of the plurality of sensors 14 from moving, when the inner cartridge 15 is in motion. As will be further discussed below, during the operation of the sensor-dispensing device, the inner cartridge 15 moves in the direction of the opening 20. During this movement, the holding mechanism 24 contacts the upper most test sensor and holds the test sensor in place while the remainder of the stack of sensors 14 moves with the inner cartridge 15.

The movement of the inner cartridge 15 within the outer cartridge 13 is guided by a guiding mechanism 25. The guiding mechanism 25 ensures that the inner cartridge 15 moves in a linear fashion during the operation of the sensor-dispensing device. The feature 25 has a triangular profile that provides a linear motion for the inner cartridge 15.

As shown in FIG. 1, the plurality of test sensors 14 is stacked within the inner cartridge 15. The plurality of test sensors 14 is adapted to assist in testing at least one analyte. As discussed above, one of the analytes that may be tested is glucose from, for example, a whole blood sample. In one embodiment, the plurality of test sensors 14 would include an appropriately selected enzyme to react with the desired analyte or analytes to be tested. An enzyme that may be used to react with glucose is glucose oxidase. It is contemplated that other enzymes may be used such as glucose dehydrogenase. An example of a test sensor 14 is disclosed in U.S. Pat. No. 6,531,040 assigned to Bayer Corporation. It is contemplated that other test sensors may be used in the cartridge assembly 10.

The plurality of test sensors 14 may vary in number than shown in FIG. 1 so as to address the needs of different users. Typically, the stacked test sensors contain from about 10 to about 100 sensors. Because of limited shelf- and use-life of the test sensors, it is envisioned that a user who tests infrequently would likely desire a cartridge having less test sensors compared to a user who tests more frequently.

To urge the stacked test sensors 14 upwardly, a mechanical mechanism 16 is used according to one embodiment. The mechanical mechanism 16 is located within the inner cartridge 15, and assists in positioning one of the plurality of test sensors for eventual ejection from the cartridge 11 via opening 20. The mechanical mechanism is any device that can exert pressure on the stacked test sensors 14 so as to position one of the plurality of test sensors for ejection. For example, the mechanical mechanism 16 depicted in FIG. 1 is comprised of two springs and a sensor pressure plate 17 that guides the stack of sensors in an upwardly manner. Various types of springs may be used as the mechanical mechanism to upwardly urge the stacked test sensors 14. For example, the spring may be a compression spring or a torsion spring. Springs are desirable because of their simplicity and ease of use. Certain embodiments of the invention may have a single spring as part of the mechanism 16, while others (like the one exemplified in FIG. 1) may have two springs as part of the mechanism 16.

To assist in protecting the reagent(s) in the test sensors 14, desirable packaging material and/or desiccant material may be used. The disposable cartridge 11 is typically packaged in material that prevents or inhibits air from entering into an interior of the inner cartridge 15 that contains the test sensors 14. One type of removable packaging that may be used to enclose the disposable cartridge 11 is aluminum foil. It is contemplated that other types of removable packaging may be employed. It is contemplated that desiccant material may be added in the interior of the removable packaging to assist in maintaining an appropriate humidity level therein. If the reagent in the test sensors is not humidity sensitive, then there is little or no need to include much, if any, desiccant. The removable packaging with or without the desiccant material assists in increasing the shelf-use of the test sensors. The removable packaging is to be removed before the cartridge 11 is attached to the end cap 12.

It is contemplated that the disposable cartridge 11 may be initially placed in a polymeric container such as a bottle or other type of container. The container may be shaped similarly to the disposable cartridge with a desirable seal to prevent or inhibit air or moisture from entering the interior of the container. The container may include a lid that is attached to the remainder of the container via a living hinge. It is contemplated that desiccant may also be added within the container. The container with or without the desiccant material assists in increasing the shelf-use of the test sensors. The disposable cartridge 11 is removed from the container before being placed into the sensor-dispensing device.

Desiccant material 26 is desirably added to the disposable cartridge 11 to assist in maintaining an appropriate humidity level within the interior of the inner cartridge 15 that contains the test sensors 14. In certain embodiments of the invention the dessicant material 26 may be added to the space between the outer cartridge 13 and inner cartridge 15 as exemplified in FIG. 1. Specifically, some moisture may enter the interior of the outer cartridge 13 whenever the seal door 19 is opened and a sensor is pulled out from the inner cartridge 15, but such moisture is desirably absorbed by the desiccant material 26 so as to protect the reagent in the test sensors from degradation. By maintaining an appropriate humidity level, reagent material in the test sensors is protected. The amount of desiccant material 26 should be sufficient to obtain the desired shelf-life (the time period before any of the plurality of test sensors are used). More specifically, the shelf-life typically refers to the time period before the cartridge 11 is removed from the packaging material, if used. The amount of desiccant material 26 should also be sufficient to obtain the desired use-life (the time period after first use of one of the plurality of test sensors). More specifically, the use-life typically refers to the time period after the cartridge 11 is removed from the packaging material, if used.

Examples of desiccant that may be included within the disposable container, the removable packaging enclosing the disposable container, or the container containing the disposable cartridge 11 include commercially available desiccants. The desiccant may be in the form of several shapes including balls, tablets, granular, or paper. For example, the desiccant may be molecular sieve spheres or thick desiccant paper. A non-limiting example of desiccant material may be purchased from Multisorb of Buffalo, N.Y. in the form of, for example, molecular sieve beads. In certain embodiments of the invention, the outer cartridge may be coated with desiccant or alternately could be made of a desiccant material.

It is contemplated that desiccant may not be used for test sensors that are not humidity sensitive. The amount of desiccant used, if any, depends on how humidity sensitive the test sensor is and the duration of the desired use-life.

The seal door 19 is adapted to move from a closed position (shown in FIG. 1) to an open position (shown in FIGS. 2a-2d and FIGS. 3a-3b). In a closed position, the seal door 19 seals the interior of the cartridge 11 such that the environment and any moisture in it is prevented from contacting the test sensors 14. In such a closed position, the seal door 19 provides a substantially moisture-proof and a substantially air-tight cartridge. The seal door 19 is desirably designed to prevent or inhibit moisture from entering via the opening 20 and affecting the plurality of test sensors 14 for at least the shelf-life and use-life of the plurality of sensors. When the seal door 19 is in an open position, the test sensors 14, one at a time, can be moved through the opening 20 so as to eventually exit via the opening 20.

The end cap 12 may be made of a variety of materials, but is typically made of polymeric material. Some examples of polymeric materials that may be used in forming the end cap 12 include polycarbonate, ABS, nylon, polystyrene, polypropylene, or combinations thereof. Other additives may be added in forming the housing such as, for example, TEFLON® for lubrication or glass to provide strength. It is contemplated that other additives may be employed. Polycarbonate is desirable for several reasons including being a durable material and having an ability to prevent or inhibit air (especially oxygen and moisture) from entering the end cap 12, which in turn can enter the cartridge 11 when the seal door 19 is opened. Additionally, if the outer cartridge is formed from two distinct sections, polycarbonate is capable of sealing to itself. This may be desirable in a process where the two cartridge sections are sonically welded.

The end cap 12 may be formed by processes known to those skilled in the art including injection-molding processes. If injection-molding processes are used, the wall thicknesses are typically designed within normal ranges. It is contemplated that other processes may be used such as a molding process.

Figure 2A:
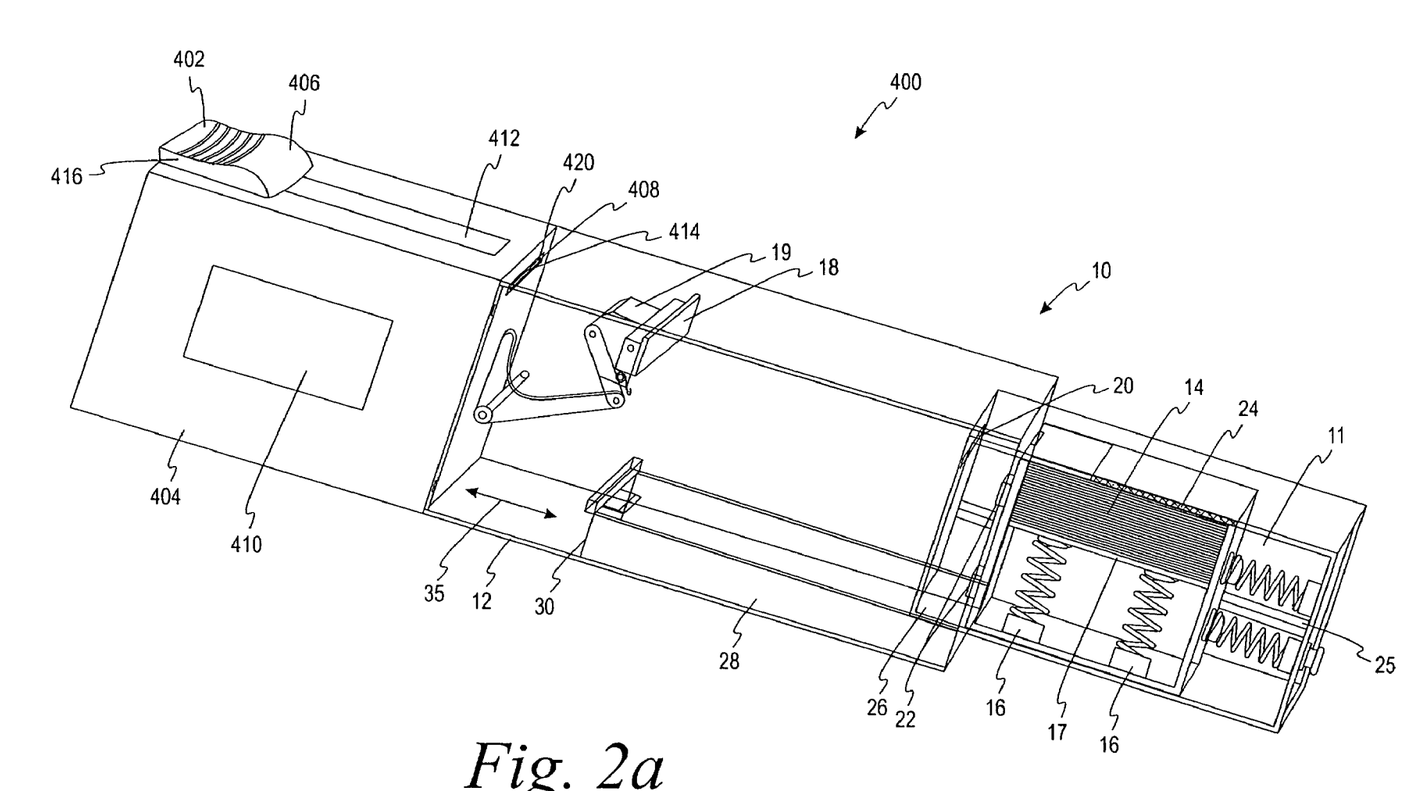
FIG. 2a is a top perspective view of the sensor-dispensing device according to an embodiment of the invention attached to the cartridge assembly of FIG. 1, where the gripping mechanism of the sensor-dispensing device is in a first position and the outer cartridge is in a first position.

Referring to FIG. 2a, a sensor-dispensing device 400 is depicted according to one embodiment. The sensor-dispensing device is used to determine concentrations of analytes. Analytes that may be measured using the present invention include glucose, lipid profiles (e.g., cholesterol, triglycerides, LDL and HDL), microalbumin, hemoglobin A1C, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, or other body fluids like ISF (interstitial fluid) and urine.

Figure 2B:
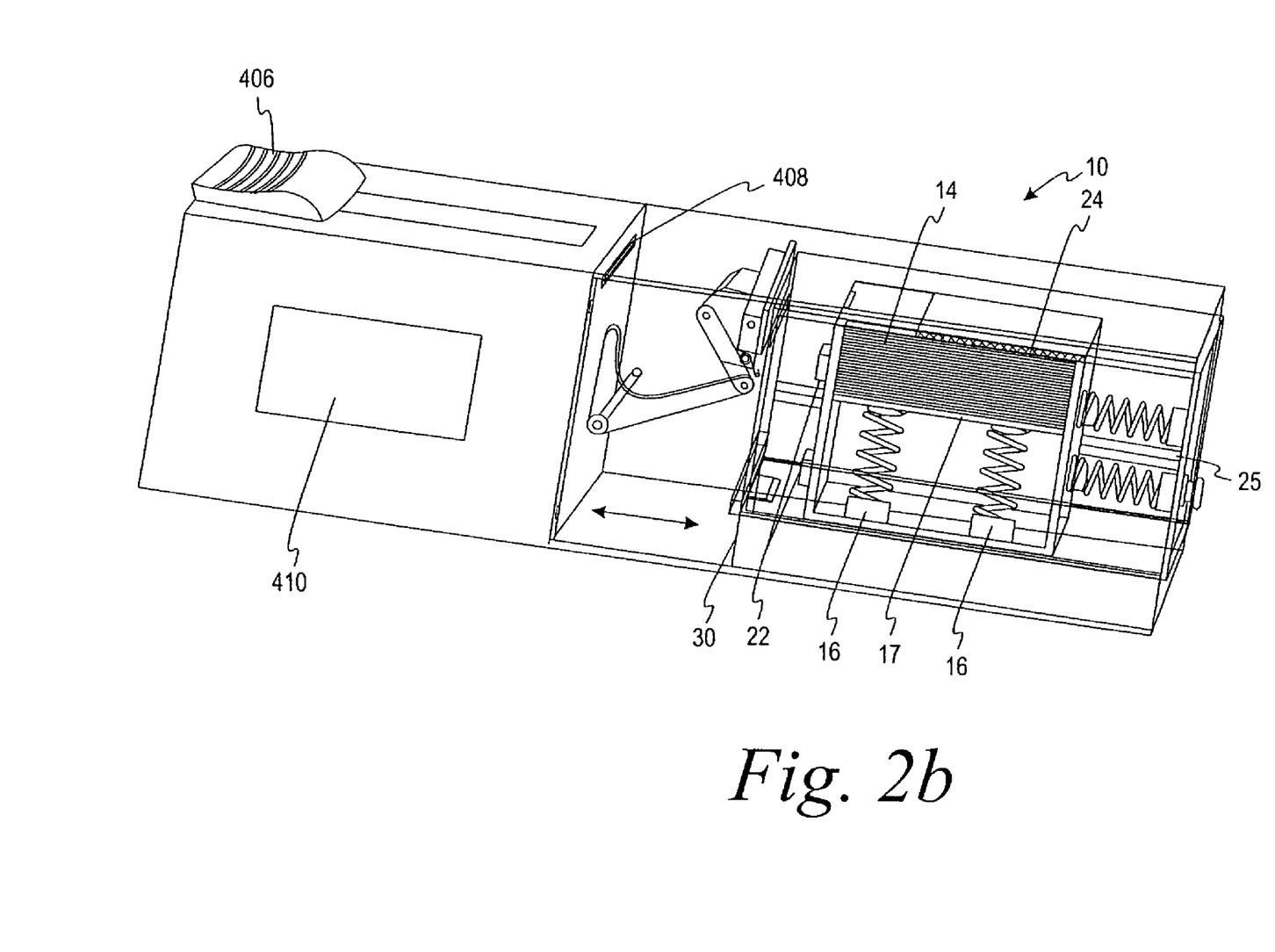
FIG. 2b is a top perspective view of the sensor-dispensing device according to an embodiment of the invention attached to the cartridge assembly of FIG. 1, where the gripping mechanism of the sensor-dispensing device is in the first position and the outer cartridge is in a second position.
Figure 2C:
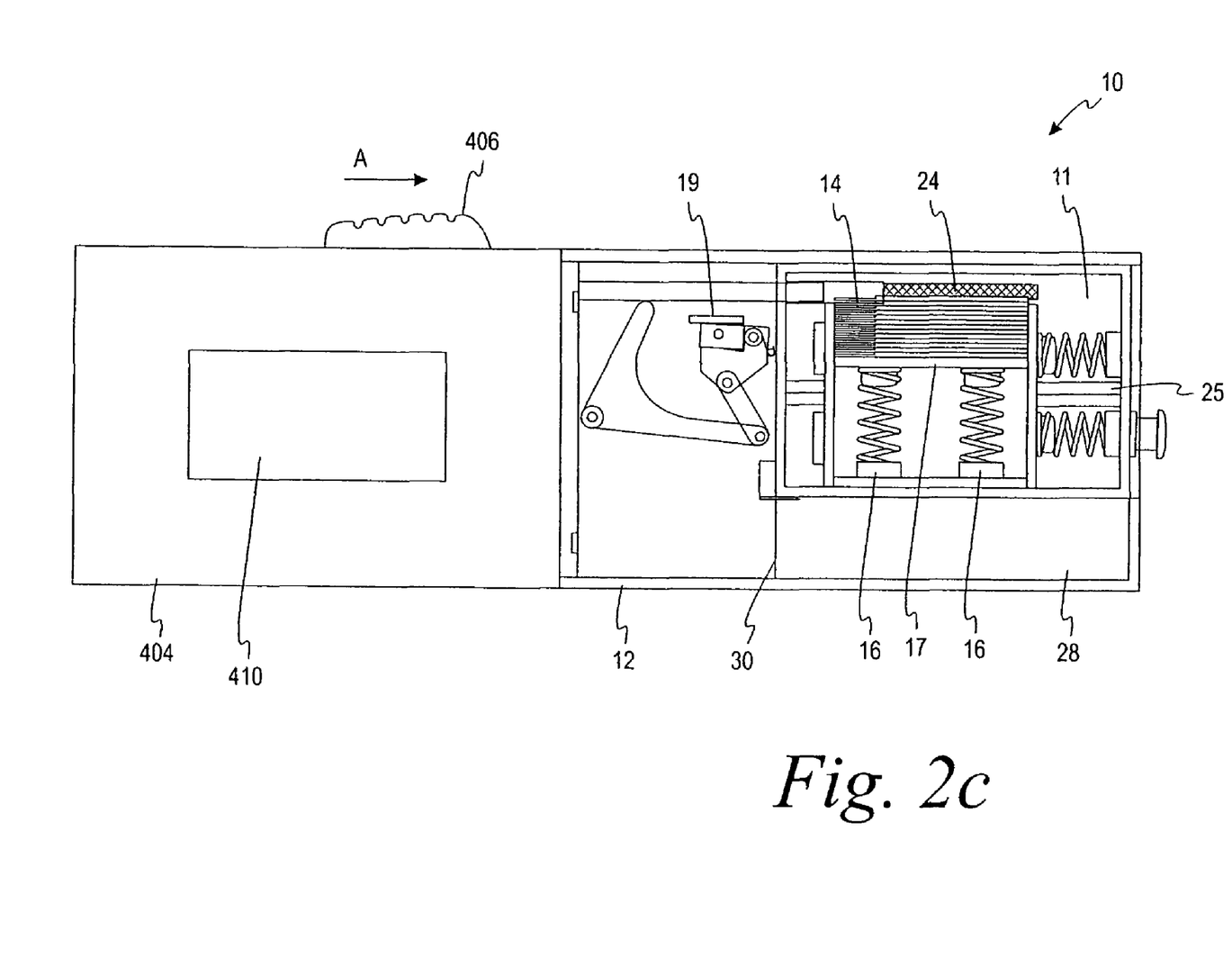
FIG. 2c is a front view of the sensor-dispensing device according to an embodiment of the invention attached to the cartridge assembly of FIG. 1, where the gripping mechanism of the sensor-dispensing device is in a second position and the outer cartridge is in the second position.
Figure 2D:
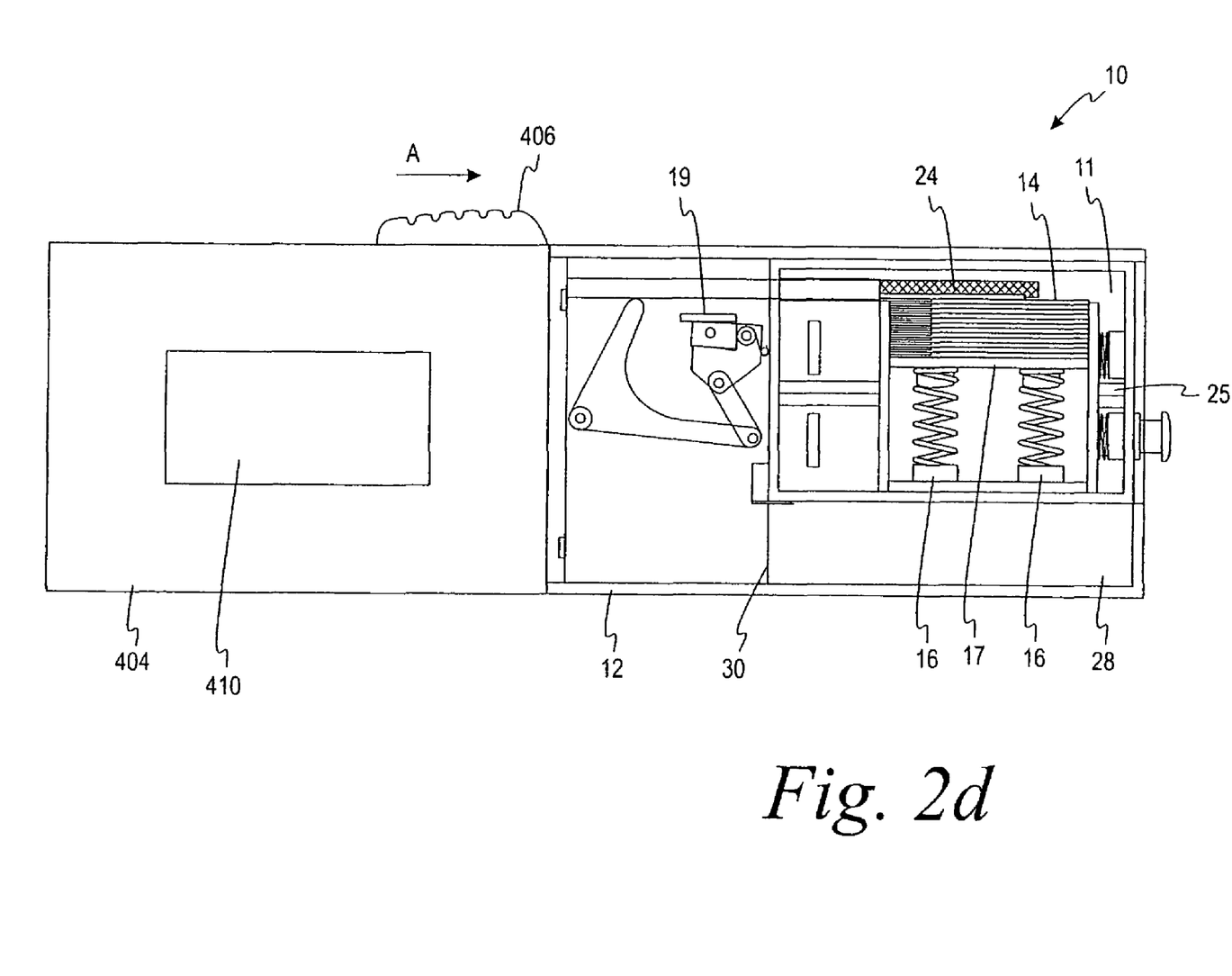
FIG. 2d is a front view of the sensor-dispensing device according to an embodiment of the invention attached to the cartridge assembly of FIG. 1, showing the contacting of the sensor by the gripping mechanism.

The sensor-dispensing device 400 comprises a cartridge assembly 10, a sliding assembly 402, and device housing 404. As shown in FIG. 2a, the sliding assembly 402 includes a slider 406 and a gripping mechanism 408 attached to the slider 406. As shown in FIGS. 2b-2d, the device housing 404 is adapted to receive the cartridge assembly 10. It is desirable for the cartridge assembly 10 to be removed from and loaded into the device housing 404 of the sensor-dispensing device 400 in a simple and easy manner. The device housing may comprise an LCD screen 410 that displays a reading that is proportional to the quantity of the particular analyte being measured. The device housing 404 as shown in FIGS. 2a-2d loads the cartridge assembly 10 on to the end of the housing 404 from which the gripping mechanism 408 extends towards the cartridge 11. Instead of being a side-loading device, the device housing may be a bottom-loading device.

It is contemplated that other cartridges and cartridge assemblies may be used. Depending on the shape of the cartridge to be used, the interior of the device housing may be redesigned to correspond to the shape of the cartridge.

Referring to FIG. 2a, the slider 406 is shown in a first position. By continuing to manually move the slider 406 in a forward direction (direction of arrow A in FIG. 2c), the slider 406 is moved to a second position (see FIG. 2d). The slider 406 in FIG. 2d is located closer to the cartridge assembly 10 than the slider 406 of FIG. 2c.

Figure 3A:
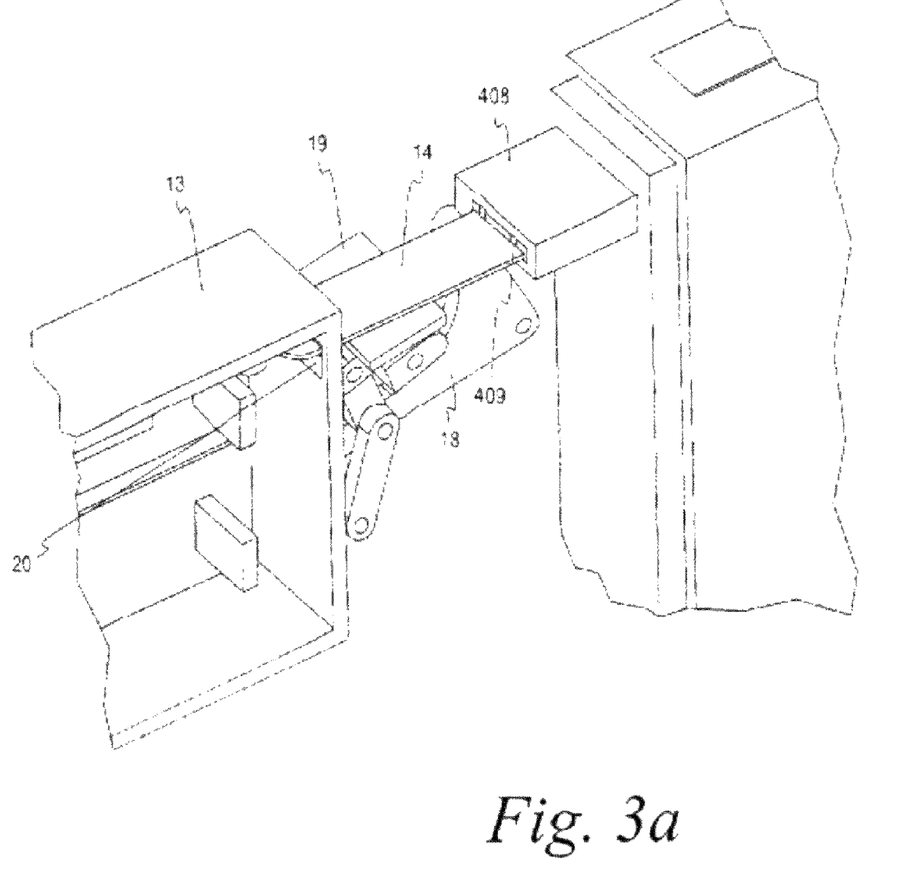
FIG. 3a is an enlarged top perspective view of the sensor-dispensing device according to an embodiment of the invention attached to the cartridge assembly of FIG. 1, showing the gripping and removal of the sensor through the outer cartridge (inner cartridge and end cap not shown)

The sliding assembly 402 is adapted to grip one of the plurality of test sensors 14 from the inner cartridge 15 and pull it at least partially through the sealing mechanism 18, such as shown in FIG. 3a. When the slider 406 is in the first position (FIGS. 2a,b), the gripping mechanism 408 (which is also in its first position in FIGS. 2a,b) does not contact any of the plurality of test sensors 14 and is contained almost entirely with the housing 404. As the slider 406 is moved in a forward direction (see direction of arrow A in FIG. 2c), the gripping mechanism 408 (see FIGS. 2c,d) is also moved in a forward direction.

Referring back to FIG. 2a, the exterior of the housing 404 forms an external channel 412 on the upper portion of the housing 404. To facilitate easy movement of the slider, the slider 406 of FIG. 2a is guided along the external channel 412 (see FIG. 2c). The slider 406 is connected to the gripping mechanism via a connecting mechanism (not shown), such that the movement of the slider 406 is always accompanied by the movement of the gripping mechanism 408. To enable easier gripping by the user, the slider 406 may form ridges or serrations on a top surface thereof such as shown in FIGS. 2a,b.

Referring back to FIG. 2a, the gripping mechanism 408 is located in an internal channel 414 that assists in facilitating and guiding the movement and positioning of the gripping mechanism 408 from a first position (FIGS. 2a,b) to a second position (FIGS. 2c,d and FIGS. 3a,b) and back to the first position. The sliding assembly 402 also includes a guiding block 416 to further ensure that the gripping mechanism 408 is moving in a proper plane. The guiding block 416 is located below the slider 406, and moves along the internal channel 414 with the gripping mechanism 408. In certain embodiments of the invention, the guiding block 416 is the connecting mechanism by which the slider 406 is connected to the gripping mechanism 408.

According to one process, the gripping mechanism 408 of FIG. 2a extends through an opening 420 in the housing and then extends towards and contacts the linkage mechanism 21 (FIG. 1). Upon contacting the linkage mechanism 21, the gripping mechanism 408 extends further towards the cartridge opening 20. The contacting of the linkage mechanism 21 and the continued forward movement of the gripping mechanism 408 causes the movement of the seal door 19 so as to unseal the opening 20 (FIG. 2c). The gripping mechanism 408 continues to move through the opening 20 and subsequently contacts the inner cartridge 15. After contacting the inner cartridge, the gripping mechanism continues to move forward until it contacts one of the plurality of test sensors 14 (see FIGS. 2c,d).

As shown in FIG. 2a, a fixed gap 35 may exist between the stop member 30 and the opening 420. As explained further below, the stop member stops the forward movement of the cartridge 11 when the gripping mechanism grips and pulls a single sensor from the stack of sensors 14 located within the inner cartridge 15. The fixed gap 35 provides a space for the test sensor after it has exited the cartridge 11. Another use for the fixed gap 35 is to provide a location for the placement of a lancet in the sensor-dispensing device 400.

The opening 420 properly aligns the gripping mechanism 408 with respect to the seal 18, as well as one of the plurality of test sensors 14. As the slider 406 is moved in a forward direction, the gripping mechanism 408 contacts and grips one of the plurality of test sensors 14 through seal 18. As the slider 406 is moved to the second position (see FIGS. 2c,d), the gripping mechanism 408 continues to grip one of the plurality of test sensors 14 that is held down in place by the holding mechanism 24. After the gripping mechanism 408 has gripped one of the plurality of test sensors 14, the slider 406 is moved back to the first position. As the slider 406 moves back to the first position, the gripping mechanism 408 continues to grip and pull one of the plurality of test sensors 14 until the sensor has been separated from the stack of the plurality of test sensors 14, and has at least partially passed through the seal 18 (see FIGS. 3a,b). As the gripping mechanism 408 grips and pulls one of the plurality of test sensors 14, the inner cartridge 15 comprising the stack of sensors begins to move towards the housing 404 (see FIG. 2c). The movement of the cartridge 11 towards the housing 404 is stopped by the stop member 30 where it latches in place. When the forward movement of the cartridge 11 is stopped by the stop member 30, the gripping mechanism 408 separates the single sensor from the stack of sensors 14. After the slider 406 has returned to the first position, the gripping mechanism 408 retains the sensor within its grasp and presents the sensor in a manner suitable for use by a user (see FIG. 4).

The movement of the inner cartridge 15 during the gripping and pulling of test sensor 14, is stopped by the features 22 on the inner surface of the outer cartridge, which prevent the inner cartridge wall from contacting the inner wall of the outer cartridge (see FIG. 1).

In a certain embodiment of the invention, the gripping mechanism 408 comprises electrical contacts 409 (see FIG. 3a) that link the sensor 14 to the meter electronics (not shown) contained within the housing 404. The sensor 14 may be linked to the meter electronics via sliding contacts or via flexible circuit cables (not shown).

Figure 4:
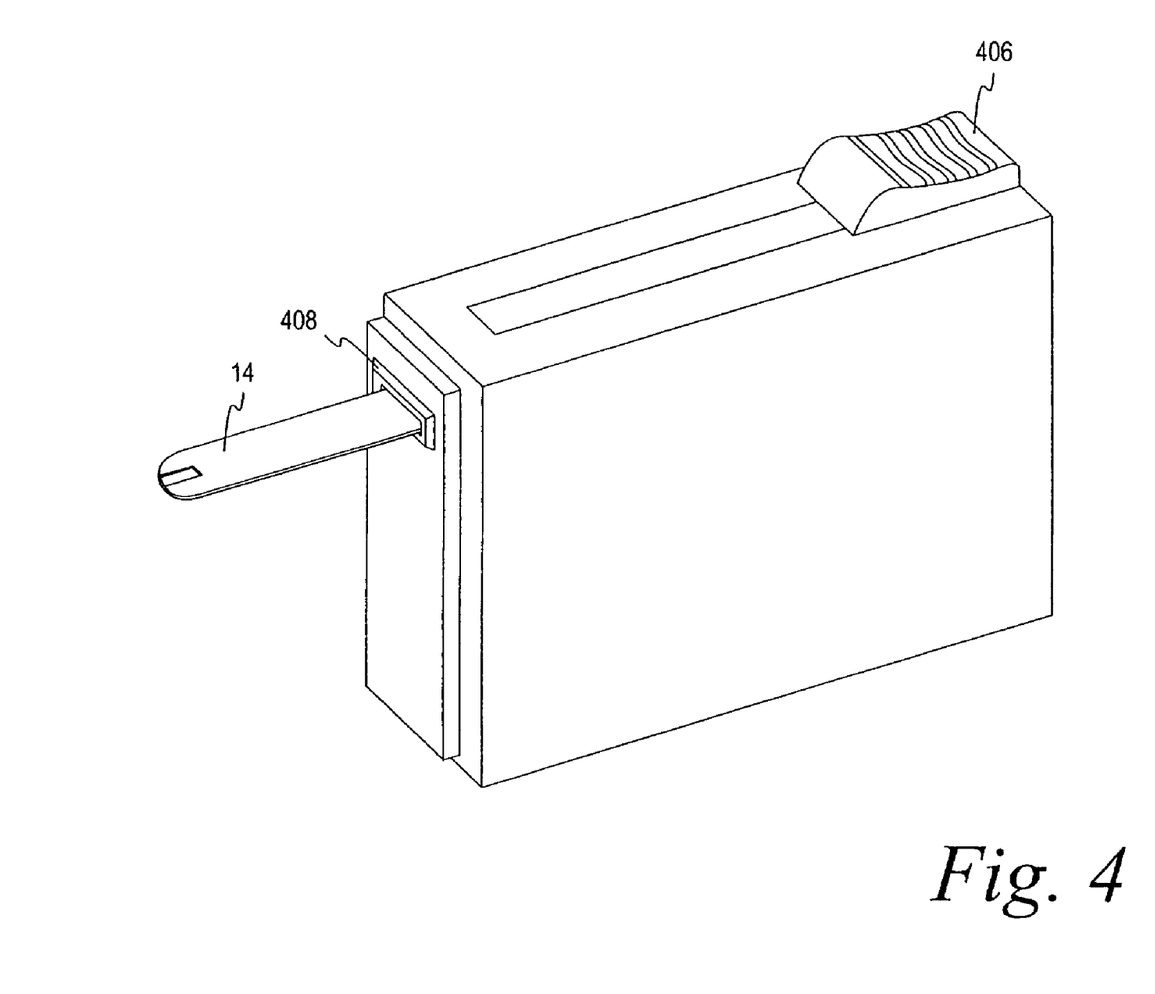
FIG. 4 is a top perspective view of the sensor-dispensing device of FIG. 2a detached from the cartridge assembly.

FIG. 4 depicts the sensor dispensing device 400 in which the housing 404 has been separated from the cartridge assembly 10. As shown in FIG. 4, after a single test sensor 14 has been separated and extracted from the plurality of test sensors located within the inner cartridge 15, the slider 406 is returned to the first position and the gripping mechanism 408 retains the sensor within its grasp and presents the sensor in a manner suitable for use by a user.

In certain embodiments of the invention, the sensor is presented in a side-wise orientation after extraction from the cartridge.

The testing end of the sensor is adapted to be placed into contact with the fluid sample (e.g., a whole blood sample) to be tested. The whole blood sample may be generated by a lancing device such as a lancet. The whole blood sample may be obtained by a lancet that may be separate from the sensor-dispensing device or may be integrated within the sensor-dispensing device. The lancing device may obtain blood by, e.g., pricking a person's finger.

According to one process, the whole blood sample may be prepared for testing by (a) advancing one of the test sensors in position to receive a whole blood sample; (b) generating a whole blood sample; and (c) bringing the test sensor and the whole blood sample into contact wherein the blood is generally drawn into the sensor by capillary action.

The sensors are typically provided with a capillary channel that extends from the front or testing end of the sensors to biosensing or reagent material disposed in the sensor. When the testing end of the sensor is placed into fluid (e.g., blood that is accumulated on a person's finger after the finger has been pricked), a portion of the fluid is drawn into the capillary channel by capillary action. The fluid then chemically reacts with the reagent material in the sensor so that an electrical signal indicative of the blood glucose level in the blood being tested is supplied and subsequently transmitted to an electrical assembly.

After the testing has been completed, the test sensor may be removed by several methods from the housing 404. In one embodiment, the sensor-dispensing device may include a eject mechanism that ejects the used test sensor from the sensor-dispensing device. In such an embodiment, the test sensor is released forcefully. In another embodiment, the test sensors may be ejected by releasing a grip of the test sensors, resulting in the test sensor being discarded by gravity from the sensor-dispensing device. In a further embodiment, the test sensor may also be removed manually from the sensor-dispensing device.

Figure 3B:
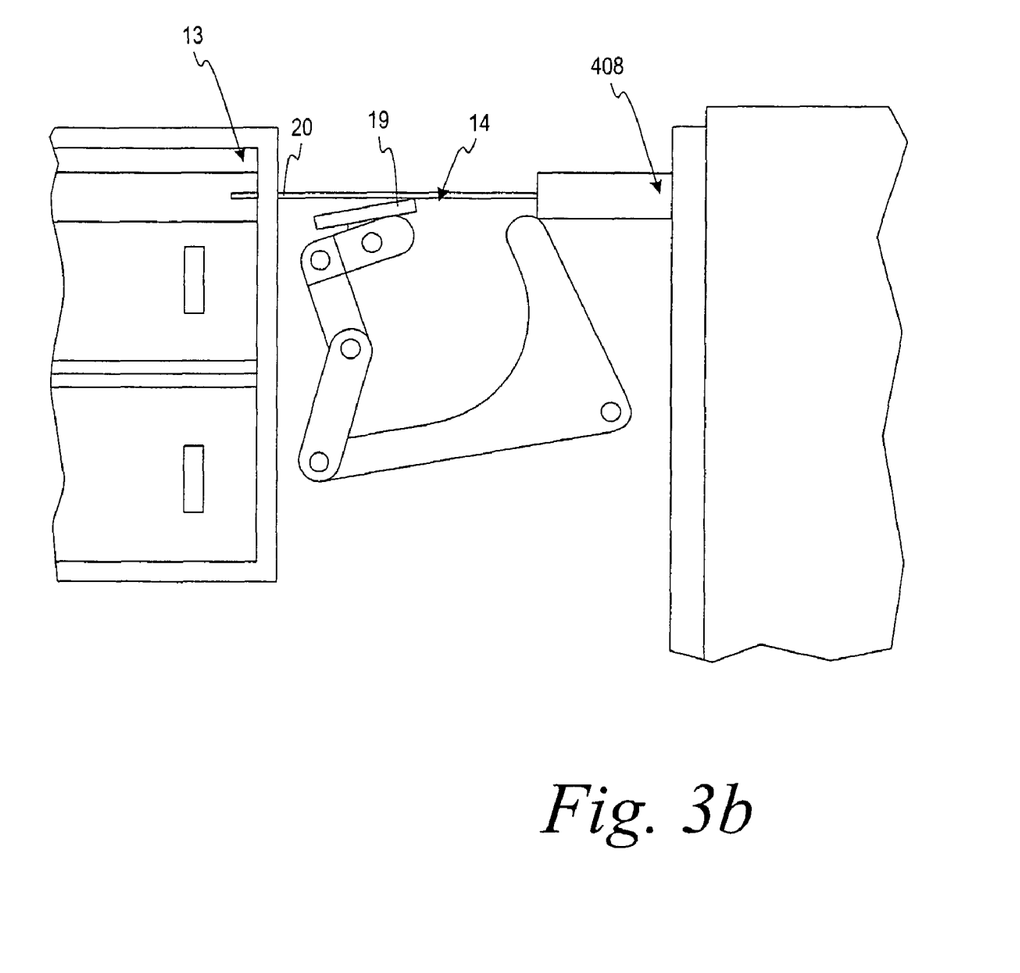
FIG. 3b is an front perspective view of the sensor-dispensing device according to an embodiment of the invention attached to the cartridge assembly of FIG. 1, showing the gripping and removal of the sensor through the outer cartridge (inner cartridge and end cap not shown)

As shown in FIGS. 3a,b, the gripping mechanism 408 may extend through the opening 20 in the cartridge when being moved to the second position. In this extended position, the gripping mechanism 408 contacts and grips one of the test sensors 14.

When the slider 406 is moved in a backward direction (i.e., the opposite direction of arrow A shown in FIG. 2c) from its second position to the first position of FIG. 2a, the gripping mechanism 408 is simultaneously moved from its second position to the first position, resulting in the gripping mechanism 408 passing through the seal 18. While the slider 406 and the gripping mechanism 408 are in the first position, the cartridge 11 is substantially moisture-proof and air-tight. It is contemplated that the sensor-dispensing device may activate the slider mechanism automatically such as in response to pressing a button.

The housing 404 and the slider 406 are typically made of a polymeric materials. Non-limiting examples of polymeric materials include polycarbonate, ABS, nylon, polypropylene, or combinations thereof. Additives may be added to the polymeric material that forms the slider. It is contemplated that the slider may be made of other materials such as metallic materials.

The gripping mechanism 408 may be made of metal or polymeric material. Some non-limited metallic materials include stainless steel and bronze with appropriate plating. Non-limiting examples of polymeric materials include polycarbonate, ABS, nylon, polypropylene, or combinations thereof. Additives may be added to the polymeric material that forms the gripping mechanism.

The sensor-dispensing device 400 typically includes a microprocessor or the like for processing and/or storing data generated during the blood glucose test procedure. This data may be displayed on a liquid crystal display 410 located on the surface of the housing 404 (see FIG. 2a). The liquid crystal display displays information from the testing procedure on the sensor-dispensing device 400.

Some of the information that may be displayed when the sensor-dispensing device is in use include the following: a battery indication, a numerical display, an indication of the number of sensors remaining, an indication to load a cartridge into the sensor-dispensing device, apply blood indication, a temperature indication, or various combinations thereof.

The sensor-dispensing device 400 may also contain an opening for a battery-tray assembly. The battery-tray assembly includes a battery-tray in which a battery is disposed. The battery-tray assembly is inserted into the opening in a side of the sensor-dispensing device 400. When so inserted, the battery provides power for the electronics within the device 400, including the circuitry on the circuit board assembly (not shown) and the liquid crystal display 410.

While the invention has been described with reference to details of the illustrated embodiment, these details are not intended to limit the scope of the invention as defined in the appended claims. For example, the sensor-dispensing device 400 can be used for testing fluids other than blood glucose. In fact, the sensor-dispensing device 400 can be used in connection with the analysis of any type of chemistry fluid that can be analyzed by using a reagent material.

Alternative Embodiment A

A sensor-dispensing device adapted to determine an analyte concentration of a fluid, the device comprising:

a cartridge assembly including an end cap, a disposable cartridge and a sealing mechanism, the disposable cartridge comprising an outer cartridge and an inner cartridge, the inner cartridge containing a plurality of sensors arranged in a stack therein, the outer cartridge including a holding mechanism that holds at least one of the sensors in place during movement of the inner cartridge, the sealing mechanism being adapted to form a substantially moisture-tight seal so as to protect the sensors within the inner cartridge from atmospheric moisture; and a gripping mechanism being adapted to grip a sensor and pull the sensor from the stack through the opening in the outer cartridge to a dispensed position, wherein the outer cartridge forms an opening of sufficient dimensions to permit a sensor and the gripping mechanism to pass therethrough.

Alternative Embodiment B

The sensor-dispensing device of embodiment A further comprising a mechanism for determining the analyte concentration in the fluid

Alternative Embodiment C

The sensor-dispensing device of embodiment A wherein the gripping mechanism is reciprocally slidable between a first position and a second position.

Alternative Embodiment D

The sensor-dispensing device of embodiment C wherein the movement of the gripping mechanism from the first position to the second position causes the gripping mechanism to insert at least a portion thereof between a sealing surface and the sealing mechanism so as to break the seal and then to travel to an extent sufficient to permit a sensor to be urged to a position to contact the sensor and wherein the movement of the gripping mechanism from the second position to the first position pulls the sensor through the opening.

Alternative Embodiment E

The sensor-dispensing device of embodiment D wherein the gripping mechanism contacts both the sealing mechanism and an uppermost sensor in the stack when traveling from the first position to the second position.

Alternative Embodiment F

The sensor-dispensing device of embodiment E wherein the gripping mechanism is adapted to be manually urged between the first and second positions by a user.

Alternative Embodiment G

The sensor-dispensing device of embodiment A wherein the sealing mechanism is attached to the end cap.

Alternative Embodiment H

The sensor-dispensing device of embodiment G wherein the sealing mechanism includes a seal door and a linkage mechanism, the linkage mechanism assists in facilitating the movement of the seal door.

Alternative Embodiment I

The sensor-dispensing device of embodiment A wherein the dimensions of the opening permit only a single sensor at a time to be pulled therethrough.

Alternative Embodiment J

The sensor-dispensing device of embodiment A wherein the outer housing includes exactly one opening.

Alternative Embodiment K

The sensor-dispensing device of embodiment A wherein the holding mechanism holds the uppermost sensor in place while the inner cartridge is moved relative to the outer cartridge by the gripping mechanism.

Alternative Embodiment L

The sensor-dispensing device of embodiment A wherein the gripping mechanism contains electrical contacts to link the sensor to the electronics of the sensor-dispensing device.

Alternative Embodiment M

A cartridge assembly being adapted to be used in a sensor-dispensing device, the sensor-dispensing device being adapted to determine the analyte concentration of a fluid, the cartridge assembly comprising:
an end cap;
a disposable cartridge comprising an outer cartridge and an inner cartridge, the inner cartridge containing a plurality of sensors arranged in a stack therein, each of the plurality of sensors carrying a reagent sufficient to produce a signal in response to the analyte concentration in the fluid, the outer cartridge forming an opening of sufficient dimensions to permit a sensor to pass through the opening, the outer cartridge including a holding mechanism that holds at least one of the sensors in place during movement of the inner cartridge; and
sealing mechanism being adapted to form a substantially moisture-tight seal so as to protect the sensors within the inner cartridge from atmospheric moisture.

Alternative Embodiment N

The cartridge assembly of embodiment M wherein the sealing mechanism is attached to the end cap.

Alternative Embodiment O

The cartridge assembly of embodiment N wherein the sealing mechanism includes a seal door and a linkage mechanism, the linkage mechanism assists in facilitating the movement of the seal door.

Alternative Embodiment P

The cartridge assembly of embodiment M wherein the dimensions of the opening permit only a single sensor at a time to be pulled therethrough.

Alternative Embodiment Q

The cartridge assembly of embodiment M wherein the outer cartridge includes exactly one opening.

Alternative Embodiment R

The cartridge assembly of embodiment M further including a mechanical mechanism for positioning the test sensors, one at a time, for removal from the inner cartridge.

Alternative Embodiment S

The cartridge assembly of embodiment M wherein the holding mechanism holds the uppermost sensor in place while the inner cartridge is moved relative to the outer cartridge.

Alternative Process T

A method of operating a sensor-dispensing device, the sensor-dispensing device adapted to handle a sensor pack containing a plurality of sensors, the method comprising the acts of:

providing a sensor-dispensing device including a cartridge assembly and a gripping mechanism, the cartridge assembly including an end cap, a disposable cartridge and a sealing mechanism, the disposable cartridge comprising an outer cartridge and an inner cartridge, the inner cartridge containing a plurality of sensors arranged in a stack therein, the outer cartridge including a holding mechanism that holds at least one of the sensors in place during movement of the inner cartridge, the outer cartridge forming an opening of sufficient dimensions to permit a sensor and the gripping mechanism to pass therethrough, the sealing mechanism being adapted to form a substantially moisture-tight seal so as to protect the sensors within the inner cartridge from atmospheric moisture; and advancing the gripping mechanism so as to move the sealing mechanism to an open position and to contact one of the plurality of test sensors, pulling the test sensor via the gripping mechanism through the opening of the cartridge assembly, placing a fluid with an analyte on the test sensor; and determining the concentration of the analyte.

Alternative Process U

The method of process T wherein the analyte is glucose.

Alternative Process V

The method of process T wherein advancing the gripping mechanism includes reciprocally sliding the gripping mechanism between a first position and a second position.

Alternative Process W

The method of process T wherein the sealing mechanism is attached to the end cap.

Alternative Process X

The method of process T wherein the sealing mechanism includes a seal door and a linkage mechanism, the linkage mechanism assists in facilitating the movement of the seal door.

Alternative Process Y

The method of process T wherein the dimensions of the opening permit only a single sensor at a time to be pulled therethrough.

Alternative Process Z

The method of process T wherein the outer housing includes exactly one opening.

Alternative Process AA

The method of process T wherein the holding mechanism holds the uppermost sensor in place while the inner cartridge is moved relative to the outer cartridge by the gripping mechanism.

Alternative Process BB

The method of process T wherein the gripping mechanism contains electrical contacts to link the sensor to the electronics of the sensor-dispensing device.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as defined in the appended claims.

The invention claimed is:

1. A sensor-dispensing device adapted to determine an analyte concentration of a fluid, the device comprising:

a cartridge assembly including an outer cartridge and an inner cartridge, the inner cartridge containing a plurality of sensors arranged in a stack therein, the outer cartridge including a holding mechanism configured to engage at least one of the sensors to hold the at least one of the sensors in place during movement of the inner cartridge with respect to the outer cartridge; and a gripping mechanism external to the cartridge assembly and moveable between a first position and a second position, the gripping mechanism including an engaging end with a slot configured to engage and grip the at least one of the sensors such that a portion of the at least one of the sensors is inside the slot in response to the gripping mechanism being in the second position, the engaging end of the gripping mechanism being configured to cause the inner cartridge to move with respect to the outer cartridge in response to the gripping mechanism being moved toward the second position, the gripping mechanism being configured to extend into an opening in the outer cartridge and to pull the at least one of the sensors from the stack through the opening in the outer cartridge, the opening being of sufficient dimensions to permit the at least one of the sensors and the gripping mechanism to pass therethrough.

2. The sensor-dispensing device of claim 1, wherein the cartridge assembly further comprises an end cap and a sealing mechanism, the sealing mechanism being configured to form a substantially moisture-tight seal so as to protect the sensors within the inner cartridge from atmospheric moisture.

3. The sensor-dispensing device of claim 2, wherein the movement of the gripping mechanism from the first position to the second position causes the gripping mechanism to break the seal and then to travel to an extent sufficient to permit a sensor to be urged to a position to contact the gripping mechanism and wherein the movement of the gripping mechanism from the second position to the first position pulls the sensor through the opening.

4. The sensor-dispensing device of claim 3, wherein the gripping mechanism contacts both the sealing mechanism and an uppermost sensor in the stack when traveling from the first position to the second position.

5. The sensor-dispensing device of claim 4, further comprising a slider coupled to the gripping mechanism such that the gripping mechanism is configured to be manually urged between the first and second positions by a user via the slider.

6. The sensor-dispensing device of claim 2, wherein the sealing mechanism is attached to the end cap.

7. The sensor-dispensing device of claim 6, wherein the sealing mechanism includes a seal door and a linkage mechanism, the linkage mechanism assists in facilitating the movement of the seal door.

8. The sensor-dispensing device of claim 1, wherein the dimensions of the opening permit only a single sensor at a time to be pulled therethrough.

9. The sensor-dispensing device of claim 1, wherein the outer cartridge includes exactly one opening.

10. The sensor-dispensing device of claim 1, wherein the holding mechanism holds the uppermost sensor in place while the inner cartridge is moved relative to the outer cartridge by the gripping mechanism.

11. The sensor-dispensing device of claim 1, wherein the gripping mechanism contains electrical contacts within the slot that are configured to electrically couple the at least one of the sensors in the slot to electronics of the sensor-dispensing device.

12. A cartridge assembly being adapted to be used in a sensor-dispensing device, the sensor-dispensing device being adapted to determine the analyte concentration of a fluid, the cartridge assembly comprising:
an end cap;
a disposable cartridge comprising an outer cartridge and an inner cartridge, the inner cartridge containing a plurality of sensors arranged in a stack therein, the outer cartridge forming an opening of sufficient dimensions to permit a sensor and a gripping mechanism to pass through the opening, the gripping mechanism being external to the cartridge assembly and being configured to extend into the opening in the outer cartridge, the outer cartridge including a holding mechanism having a lip, the lip being configured to engage an end of at least one of the sensors to hold the at least one of the sensors in place during lateral movement of the inner cartridge with respect to the outer cartridge, the disposable cartridge being removably located within the end cap; and
a sealing mechanism attached within the end cap and configured to engage the disposable cartridge located within the end cap such that the sealing mechanism is adapted to form a substantially moisture-tight seal so as to protect the sensors within the inner cartridge from atmospheric moisture.

13. The cartridge assembly of claim 12, wherein the sealing mechanism includes a seal door and a linkage mechanism, the linkage mechanism assists in facilitating the movement of the seal door.

14. The cartridge assembly of claim 12, wherein the dimensions of the opening permit only a single sensor at a time to be pulled therethrough.

15. The cartridge assembly of claim 12, wherein the outer cartridge includes exactly one opening.

16. The cartridge assembly of claim 12, further comprising a mechanical mechanism positioned within the inner cartridge for positioning the test sensors, one at a time, for removal from the inner cartridge.

17. The sensor-dispensing device of claim 1, wherein the holding mechanism includes a lip, the lip being configured to engage an end of the at least one of the sensors to hold the at least one of the sensors in place during the movement of the inner cartridge with respect to the outer cartridge.

18. The sensor-dispensing device of claim 1, wherein the movement of the inner cartridge with respect to the outer cartridge is lateral.

19. The sensor-dispensing device of claim 18, wherein the lateral movement of the inner cartridge with respect to the outer cartridge and the movement of the gripping mechanism are in the same directions.

20. The cartridge assembly of claim 12, wherein the inner cartridge moves laterally with respect to the outer cartridge when the gripping mechanism is moved through the opening of the outer cartridge.

21. The sensor-dispensing device of claim 1, further comprising a mechanical mechanism positioned within the inner cartridge and adjacent to the stack such that the mechanical mechanism exerts pressure on the stack to cause the holding mechanism to engage the at least one of the sensors.

22. The sensor-dispensing device of claim 21, wherein the mechanical mechanism includes a pressure plate and at least one biasing member.

23. The sensor-dispensing device of claim 7, wherein the gripping mechanism is configured to engage the linkage mechanism to cause the sealing mechanism to move from a sealed position to an open position.

24. The sensor-dispensing device of claim 2, wherein as the gripping mechanism moves from the first position to the second position, the gripping mechanism initially enters the end cap, then moves through the opening in the outer cartridge, and then engages the inner cartridge.

25. The sensor-dispensing device of claim 24, wherein the gripping mechanism is at least partially positioned in an internal channel within a device housing coupled to the end cap in response to the gripping mechanism being in the first position.

26. The cartridge assembly of claim 12, wherein the outer cartridge encompasses the inner cartridge.

27. The cartridge assembly of claim 26, wherein the end cap encompasses the outer cartridge.

28. A method of dispensing a test sensor, comprising:
providing a sensor-dispensing device including a cartridge assembly coupled to a device housing including a gripping mechanism external to the cartridge assembly, the cartridge assembly including an outer cartridge and an inner cartridge, the inner cartridge including a plurality of sensors therein;
moving the gripping mechanism from a first position in the device housing towards a second position at least partially within the cartridge assembly, during the moving:
(1) moving an engaging end of the gripping mechanism through an opening in the outer cartridge;
(2) engaging the engaging end of the gripping mechanism with the inner cartridge;
(3) moving the inner cartridge with respect to the outer cartridge; and
(4) gripping one of the plurality of sensors with the gripping mechanism such that a portion of the one of the plurality of sensors is positioned within a slot of the engaging end of the gripping mechanism.

29. The method of claim 28, further comprising, during the moving of the gripping mechanism, engaging the engaging end of the gripping mechanism with a sealing mechanism positioned adjacent to the cartridge assembly and moving the sealing mechanism from a sealing position to an open position.

30. The method of claim 28, further comprising, during the moving of the gripping mechanism, engaging a holding mechanism positioned within the outer cartridge with the one of the plurality of sensors such that the one of the plurality of sensors is held by the holding mechanism with respect to the outer cartridge as the inner cartridge moves with respect to the outer cartridge.

31. The method of claim 28, further comprising retracting the gripping mechanism through the opening in the outer cartridge while the portion of the one of the plurality of sensors remains positioned within the slot of the engaging end of the gripping mechanism.

32. The method of claim 28, wherein the gripping further comprises engaging the one of the plurality of sensors with one or more electrical contacts positioned within the slot such that the one of the plurality of sensors is electrically coupled with electronics of the sensor-dispensing device.

33. The method of claim 28, wherein the cartridge assembly is coupled to the device housing via an end cap, the cartridge assembly being positioned within the end cap.

* * * * *